United States Patent [19]
Kobayashi

[11] Patent Number: 5,290,450
[45] Date of Patent: Mar. 1, 1994

[54] ANAEROBIC DIGESTION PROCESS FOR SEWAGE SLUDGE

[76] Inventor: Yoshio Kobayashi, 543-10 Shichiyama, Kumatori-cho, Sennan-gun, Osaka, Japan

[21] Appl. No.: 596,917

[22] Filed: Oct. 15, 1990

Related U.S. Application Data

[63] Continuation-in-part of Ser. No. 330,256, Mar. 29, 1989, abandoned.

[30] Foreign Application Priority Data

Mar. 30, 1988 [JP] Japan .................. 63-74606

[51] Int. Cl.$^5$ ............................. C02F 11/04
[52] U.S. Cl. .................. 210/603; 210/609; 210/613
[58] Field of Search ........... 210/603, 609, 613, 615, 210/631

[56] References Cited

U.S. PATENT DOCUMENTS

| | | | |
|---|---|---|---|
| 3,402,103 | 9/1968 | Amberg et al. | 210/615 |
| 3,959,125 | 5/1976 | Teletzke | 210/603 |
| 3,981,800 | 9/1976 | Ort | 210/609 |
| 4,040,953 | 8/1977 | Ort . | |
| 4,088,571 | 5/1978 | Helgesson | 210/615 |
| 4,132,638 | 1/1979 | Carlsson | 210/609 |
| 4,396,402 | 8/1983 | Ghosh | 210/613 |
| 4,400,195 | 8/1983 | Rijkens | 210/603 |
| 4,684,468 | 8/1987 | De Baere | 210/613 |

FOREIGN PATENT DOCUMENTS

| | | |
|---|---|---|
| 225983 | 8/1985 | German Democratic Rep. . |
| 60-48198 | 3/1985 | Japan . |
| 61-230797 | 10/1986 | Japan . |
| 8501281 | 3/1985 | PCT Int'l Appl. . |
| 1037683 | 8/1966 | United Kingdom . |
| 1110352 | 4/1968 | United Kingdom . |
| 2047223 | 11/1980 | United Kingdom . |

OTHER PUBLICATIONS

*Webster's Third New International Dictionary of the English Language*, p. 218 (1971).
*Biotechnology Encyclopedia*, p. 625 (1986).
*Methane Production from Agricultural and Domestic Wastes*, Hobson et al., Applied Science Publishers, Ltd., London (1981), pp. ix–xi.

Primary Examiner—Christopher Upton
Attorney, Agent, or Firm—Lowe, Price, LeBlanc & Becker

[57] ABSTRACT

An anaerobic digestion process for sewage sludge comprises a first step of dewatering the raw sewage sludge to provide a solids content therein of at least 10 weight %. A portion of digested sludge resulting from methane fermentation is recirculated and added to the dewatered raw sludge, the weight ratio of digested sludge to dewatered raw sludge being at least 1:1. The resulting mixture is homogeneously kneaded and then subjected to methane fermentation. At least one of the dewatered raw sludge prior to the recirculating step and the kneaded sludge mixture during methane fermentation is subjected to thermal treatment at a temperature not less than 50° C.

8 Claims, 5 Drawing Sheets

ANAEROBIC DIGESTION PROCESS FOR SEWAGE SLUDGE

RELATED APPLICATION

The present application is a continuation-in-part of copending application Ser. No. 07/330,256 filed Mar. 29, 1990, now abandoned.

FIELD OF THE INVENTION

The present invention relates to an anaerobic digestion process for sewage sludge.

BACKGROUND OF THE INVENTION

In general, sludge is discharged from a sewage-treatment plant in a state having a solids content of about 2 weight %. In a conventional method for reducing the amount of such discharge, the sludge is guided to a digestor chamber for methane fermentation.

In such a conventional method, however, a digestor chamber having a large capacity is required since the rate of fermentation is slow and the sludge concentration is very dilute. Further, the conventional method is inferior in economic efficiency since the sewage gas yield thereof is 40 to 50%, at most, with the result that a considerable part of the sewage gas generated through digestion is employed in heating the sludge.

In improving sludge digestion techniques, a first important goal is to reduce the size of the digestor chamber, and a second goal is to improve the heat balance, as well as the sewage gas generation efficiency, in the process. An attempt has recently been made to enrich the sludge for increasing its solids content from about 2 weight % to 4 to 6 weight %, in order to reduce the capacity of the digestor chamber and to improve the heat balance so as to be able to recover energy through a sewage gas power generation system. However, sufficient economic efficiency cannot yet be obtained through such enrichment, and further improved performance is desired.

Two methods are generally known for improving the efficiency of methane fermentation. The first method is generally referred to as "thermophilic digestion" wherein the methane fermentation is performed at a relatively high temperature greater than about 50° C., i.e., in the range of from 50° C. to 55° C. The fermentation temperature can be as high as about 65° C., although higher temperatures are avoided in order to prevent destruction of the inoculant which is employed for methane fermentation. The thermophilic digestion method is disclosed by Hobson et al, *Methane Production From. Acricultural and Domestic Wastes*, Applied Science Publishers, Ltd. (1981), pages 190, 226-228. In the thermophilic digestion method, the speed of fermentation is increased from 2 to 2.5 times that in ordinary methane fermentation conducted at a temperature of, for example, 35° C.

The second of the generally known methods for improving the efficiency of methane fermentation is referred to as "thermal pretreatment" wherein heat treatment of raw sludge is performed prior to methane fermentation. The thermal pretreatment provides increased efficiency in methane fermentation by converting organic substances which are not easily decomposed into more biodegradable organic forms. The thermal pretreatment involves heating the raw sludge to temperatures greater than about 50° C., and often temperatures in the range of from about 60° C. to about 180° C. are employed. Thermal pretreatment methods are disclosed by Hobson et al at page 188, Haug et al, "Effect of Thermal Pretreatment on Digestibility and Dewaterability of Organic Sludges," *Journal of Water Pollution Control Federation*, 50 (1), January 1978, pages 73-85, and Hiraoki et al, "Highly Efficient Anaerobic Digestion With Thermal Pretreatment," *Water Science and Technology*, Volume 17, Amsterdam (1984), pages 529-539. For example, Haug et al disclose that methane production increases 14% with the use of a thermal pretreatment at 100° C. and 60 to 70% with a thermal treatment conducted at 175° C. Hiraoki et al also disclose that gas production yield increases more than 30% with the use of a thermal pretreatment at a temperature of from 60° to 80° C.

Thus, the thermophilic digestion and thermal pretreatment methods are effective in improving the efficiency of sludge digestion. However, if the concentration of the sludge is from about 4 to 6%, the heating temperature is limited to about 30° C. since excessively large quantities of heat are required for further heating. Thus, methane fermentation cannot be advantageously conducted at a temperature of 50° to 55° C. as required in the thermophilic digestion and raw sludge cannot be advantageously heated to temperatures greater than 50° C. as required in the thermal pretreatment method in ordinary sewage treatment plants since excessively large quantities of heat are required for such treatments.

SUMMARY OF THE INVENTION

Accordingly, it is an object of the present invention to provide an anaerobic digestion process for sewage sludge, which process improves the generation efficiency of sewage gas while reducing the capacity of the digestor chamber.

The present invention provides a sewage sludge anaerobic digestion process wherein a portion of digested sludge resulting from methane fermentation is recirculated and raw sludge is added to the recirculated portion of the digested sludge to cause methane fermentation. The inventive process comprises the steps of dewatering the raw sludge to provide a solids content therein of at least 10 weight %, adding the dewatered raw sludge to the recirculated portion of the digested sludge and homogeneously kneading the same with each other. Methane fermentation of the kneaded sludge is then conducted at a predetermined temperature. At least one of the dewatered raw sludge prior to the recirculating step and the kneaded sludge mixture during methane fermentation is subjected to thermal treatment at a temperature not less than about 50° C. Thus, the process according to the present invention employs at least one of the thermophilic digestion and thermal pretreatment methods of the prior art. If the dewatered raw sludge is subjected to a thermal treatment prior to the recirculating step, it is preferred that the temperature of the thermal pretreatment is from about 60° C. to about 180° C. If the kneaded sludge mixture is subjected to thermophilic digestion, it is preferred that the thermophilic digestion is conducted at a temperature of from about 50° C. to about 55° C. Since the initial step of the present process comprises dewatering the raw sewage sludge to provide a solids content therein of at least 10 weight %, excessively large quantities of heat are not required for the thermal pretreatment and/or the thermophilic digestion steps which are also included in the present process. Thus, the present process is advantageous in improving gas generation efficiency and reducing the capacity of the digestor chamber without requiring the excessively large quantities of heat employed in the conventional methods.

According to the present invention, the raw sludge is preferably dewatered to provide a solids content of at least 15 weight %, more preferably at least 20 weight %. Furthermore, the dewatered raw sludge is preferably heated at a temperature of 60° C. to 180° C. before it is added to the digested sludge. Additionally, methane fermentation is preferably performed at a relatively high temperature of 50° to 55° C. at which a higher fermentation rate is obtained.

The present invention is also applicable to a so-called two-phase anaerobic digestion process in which the methane fermentation step is separated into an acid formation step and a methanation step. In this case, raw sludge is dewatered to provide a solids content of at least 10 weight %, and the dewatered sludge is added to a portion of digested sludge resulting from acid formation fermentation. The resulting mixture is homogeneously kneaded. The kneaded sludge is subjected to acid formation fermentation, and products of acid formation fermentation are guided to a methanation chamber to generate methane. Preferably, the products of acid formation fermentation are separated in the form of a filtrate, by filtering the digested sludge after acid formation fermentation. The products of acid formation fermentation contained in the obtained filtrate are subjected to methanation fermentation by contact with a fixed biocatalyst in the methanation chamber. The term "acid formation fermentation" indicates fermentation generating lower fatty acids, alcohols and carbon dioxide gas, etc., from organic substances contained in the sludge.

In the two-phase anaerobic digestion process, improved efficiency can be obtained by heating the dewatered raw sludge and/or fermenting at a relatively high temperature as discussed above. According to such a two-phase anaerobic digestion process, kneading high-viscosity raw sludge and seed sludge becomes easier and an even higher efficiency can be achieved.

Generally, if the solid content of a raw sludge exceeds 4 to 6 weight %, the viscosity thereof is abruptly increased; further, the consumption of stirring power of a conventional methane fermentation vessel equipped with a conventional stirrer is too large to be economical if the solid content exceeds 10 weight %. Furthermore, stirring cannot be performed by a conventional stirrer if the solid concentration exceeds 15 weight %. Therefore, it has generally been considered that a practical concentration for raw sludge is not more than 4 to 6 weight %. Thus, methane fermentation has generally not been effected using sludge having a solid content of at least 10 weight %, since such methane fermentation has been considered impossible.

The Inventor has found that, even if the solid content of raw sludge exceeds 20 weight %, methane fermentation can be efficiently made by sufficiently increasing the concentration of a ferment bacteria and uniformly and homogeneously mixing the ferment bacteria into the raw sludge. According to the present invention, a small amount of highly concentrated raw sludge is added to and homogeneously mixed with highly concentrated seed sludge, i.e., digested sludge, and the mixture is maintained at a constant temperature in a digestor chamber, thereby to cause methane fermentation.

According to the present invention, the digestor chamber can be reduced in capacity as compared with the conventional art, since raw sludge is dewatered to a solids content of at least 10 weight %. If the capacity of the digestor chamber is similar to that in the conventional art, a larger amount of raw sludge can be digested.

According to the present invention, the amount of water in the raw sludge to be heated is reduced as compared with the conventional art since the sludge has a high solids content. Therefore, according to the present invention, it is possible to perform the heat treatment of raw sludge and the high-temperature fermentation which have not been previously practical.

A sewage-treatment plant may be provided with equipment for sewage gas power generation. According to the present invention, sludge can be heated through exhaust heat generated in the power generation system. Thus, the present invention is particularly suitable for such a treatment plant.

These and other objects, features, aspects and advantages of the present invention will become more apparent from the following detailed description of the present invention when taken in conjunction with the accompanying drawings.

DETAILED DESCRIPTION

The process of the present invention and the improvements thereof are illustrated by the following examples and reference examples.

FILL AND DRAW METHOD EXPERIMENT

The present invention has been studied through a Fill and Draw method experiment.

Seed sludge was prepared by dewatering a sludge digested at 50° to 55° C. into a solids content of 15%. Raw sludge was dewatered to a solids content of 21%. Heat-treated sludge was prepared by heating the dewatered raw sludge at about 170° C. for 30 minutes.

EXAMPLE 1

Figure 1:
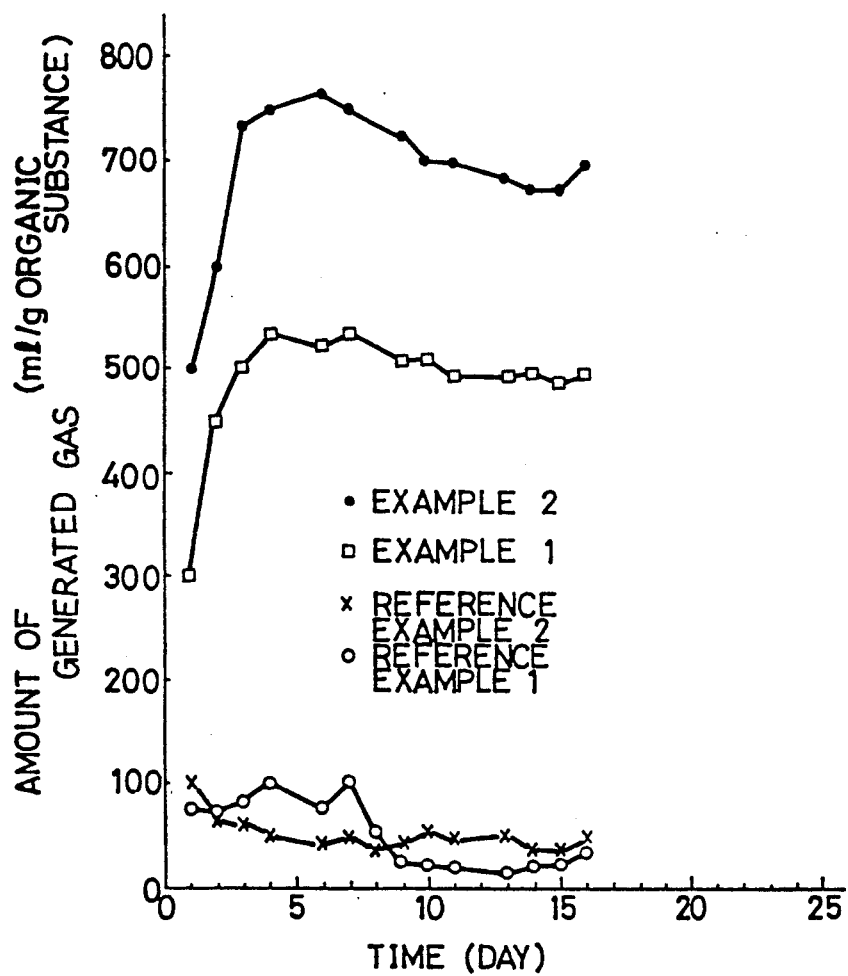
FIG. 1 illustrates the amounts of gas generated in a Fill and Draw method experiment.
Figure 2:
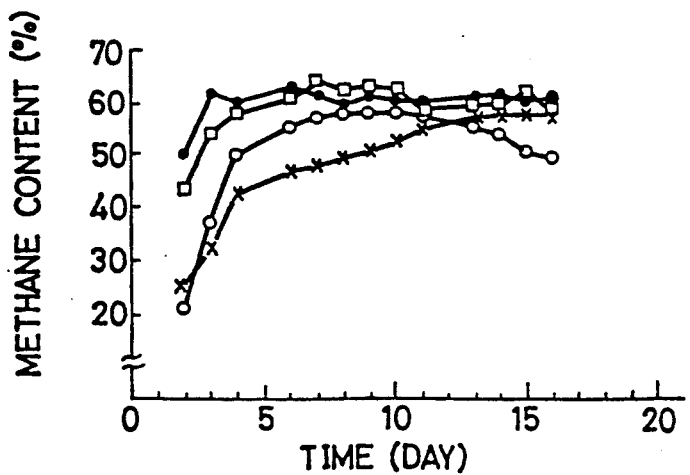
FIG. 2 illustrates methane contents in the gas generated in the Fill and Draw method experiment.

Seed sludge (200 g) and raw sludge (2.6 g) were introduced into a hermetically sealed laboratory kneader having an approximate content volume of about 1000 ml and an exhaust port, and substitution was performed in a pot of the kneader by nitrogen gas. Kneading was then performed for five minutes and thereafter the kneader was dipped and maintained in a constant-temperature water bath of 53° C. Digested gas thus generated was collected in a scavenging bottle, and the amount of generated gas and the methane content were measured the following day. Then, 2.6 g of the sludge was extracted from the pot of the kneader, and 2.6 g raw sludge was newly added and kneaded for five minutes. This operation was performed once a day, and this experiment was continued for 16 days. FIG. 1 shows the amount of generated gas and FIG. 2 shows the methane content of the generated gas.

REFERENCE EXAMPLE 1

Seed sludge (200 g) and raw sludge (2.6 g) were introduced into a 300 ml conical flask, and stirred and mixed by a glass rod with substitution in the flask with nitrogen gas. The conical flask was covered with a rubber stopper provided with a digested gas extraction port, and then maintained in a constant temperature bath of 53° C. Digested gas thus generated was collected in a scavenging bottle, and the methane content was measured on the next day. Then, 2.6 g of the sludge was extracted from the flask, and 2.6 g raw sludge was newly added and stirred and mixed by the glass rod. This operation was performed once a day, and this experiment was continued for 16 days. FIGS. 1 and 2 show the results thus obtained.

EXAMPLE 2

The raw sludge employed in Example 1 was replaced by heat-treated sludge. The amount of generated gas and the methane content in the generated gas were measured in a manner similar to Example 1. FIGS. 1 and 2 show the results.

REFERENCE EXAMPLE 2

The raw sludge employed in Reference Example 1 was replaced by heat-treated sludge, which was mixed into seed sludge and digested similarly to Reference Example 1, followed by measurement of the amount of generated gas and the methane content. FIGS. 1 and 2 show the results thus obtained.

As shown in FIG. 1, the amount of gas generated in Example 1, in which the sludge was sufficiently mixed in the laboratory kneader, was significantly higher than that of Reference Example 1, in which stirring was insufficient. The amount of generated gas is indicated in ml per g of organic substance contained in the sludge. The amount of gas generated in Reference Example 1 was at a level substantially identical to that obtained in conventional digestion performed in low concentration.

In Example 2, the raw sludge was heat-treated in advance. As shown in FIG. 1, the amount of gas generated in Example 2 was higher than that in Example 1. Thus, it is understood that the sewage gas yield was improved by the heat treatment, resulting in generation of a large amount of gas. Further, it is understood that the sludge must be sufficiently mixed also, from a comparison of Example 2 with Reference Example 2 employing the heat-treated-sludge.

Bench Scale Experiment

Figure 3:
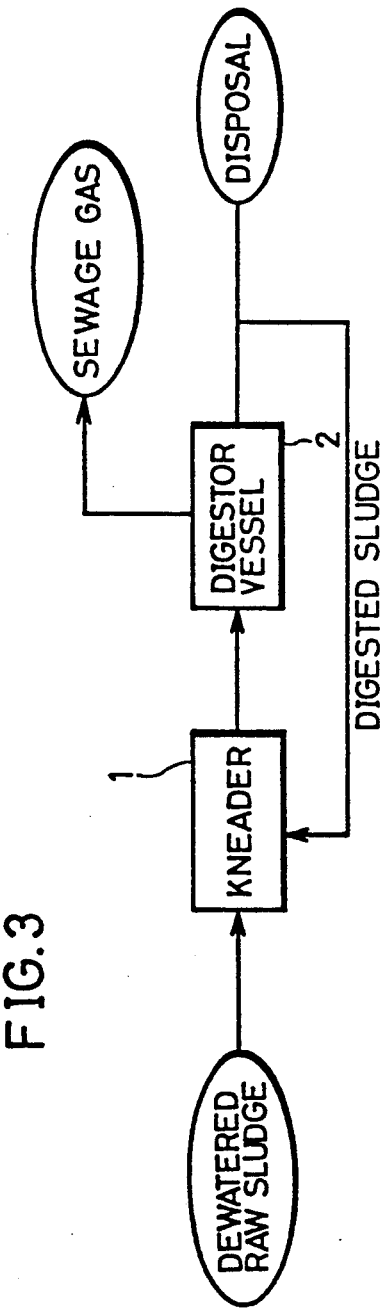
FIG. 3 is a process drawing showing a first embodiment of the present invention.

FIG. 3 is a process drawing showing a first embodiment of the present invention. Referring to FIG. 3, raw sludge dewatered to a solids content of at least 10 weight % is introduced into a kneader 1, to which a portion of the digested sludge is recirculated. The raw sludge is mixed into the digested sludge, serving as seed sludge, in the kneader 1. The kneader 1 is capable of kneading highly viscous substances, and may be a co-kneader, a ribbon mixer or a guillotine mixer, for example. Sludge obtained by kneading the raw sludge with the digested sludge in the kneader 1 is supplied to a digestor chamber 2. In the digestor chamber 2, digestion is performed and sewage gas thus generated is extracted. A great portion of the sludge digested for a predetermined period is fed back to the kneader 1, while the remaining portion is disposed. The large mixing ratio of the digested sludge/raw sludge in the kneader 1 provides stable operation. The preferable weight ratio of digested sludge to dewatered raw sludge, which depends on the efficiency of the kneader, is selected in the range of from 1 to 20.

It is said that methane fermentation is adapted to form methane through two processes of first forming organic acids, alcohols, etc., from organic substances of substrates contained in the sludge, and then forming methane from the organic acids and alcohols. If the ferment bacteria concentration in the raw sludge is low or the raw sludge is heterogeneously mixed with seed sludge and the ferment bacteria concentration is locally reduced, formation of the organic acids and alcohols becomes dominant to inhibit the activity of the methanation bacteria. The rate of methane fermentation depends on the methanation process, and it is said that methanation bacteria are extremely sensitive to the pH value and the organic acid and alcohol concentration. Therefore, it is necessary to regularly maintain a high concentration of the methanation bacteria in the raw sludge and to mix the raw sludge with the seed sludge so that concentration of the organic acid and alcohol around the methanation bacteria is not in excess of a certain limit. In such mixing of the raw sludge and the seed sludge, it is preferable to increase the initial concentration of the ferment bacteria by increasing the amount of the seed sludge to be circulated, in order to prevent an excessive increase in the concentration of organic acid and alcohol. Thus, equilibrium in a symbiotic relation between the acid forming bacteria and the methanation bacteria is maintained.

Figure 4:
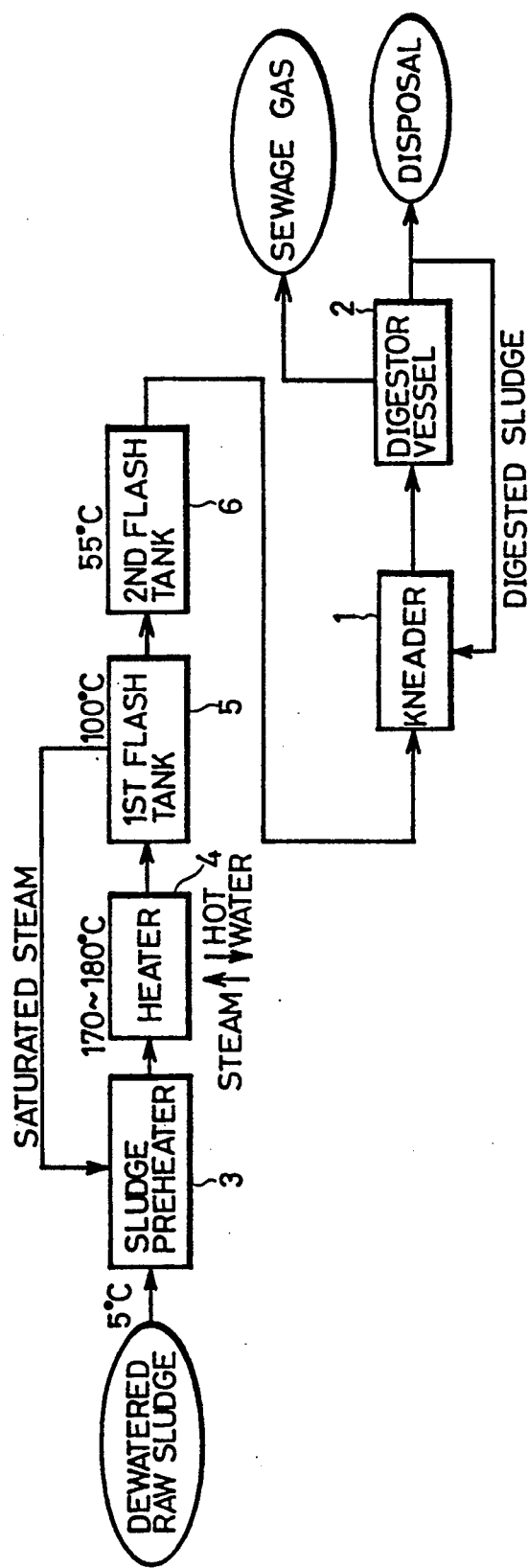
FIG. 4 is a process drawing showing a second embodiment of the present invention.

FIG. 4 is a process drawing showing a second embodiment of the present invention, in which raw sludge is heat-treated before the same is kneaded with seed sludge. Referring to FIG. 4, dewatered raw sludge is supplied to a sludge preheater 3, to be preheated therein. Then the raw sludge is supplied to a heater 4, and heated to a temperature of not less than 50° C., for example, from 60° C. to 180° C. This heater 4 can perform heating with steam, for example. Such steam heating can be made by steam recovered from waste heat of a sewage gas power generation system. The heated sludge is then introduced into a first flash tank 5, and cooled to 100° C. Saturated steam in the first flash tank 5 is fed back to the sludge preheater 1 to heat the raw sludge. Then the raw sludge is introduced into a second flash tank 6 and cooled to 55° C., for example.

The cooled raw sludge is supplied into a kneader 1, and kneaded with a recirculated digested sludge, which serves as seed sludge. The kneaded sludge is fed to a digestor chamber 2, and methane fermentation is conducted at a relatively high temperature of 50° to 55° C., for example. Sewage gas thus generated is extracted from an extracting port, and a large portion of the sludge digested for a predetermined period is fed back to the kneader 1, while the remaining portion is disposed.

Figure 5:
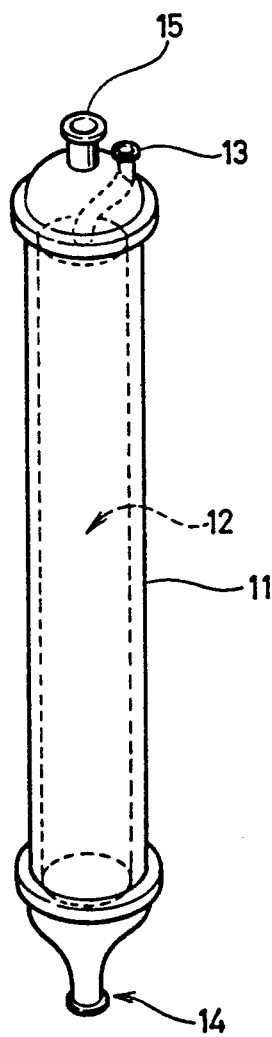
FIG. 5 is a perspective view showing a digestor chamber employed in a bench scale experiment along the process shown in FIG. 4.

The apparatus shown in FIG. 4 was employed to make a bench scale experiment. FIG. 5 shows a tube type digestor chamber employed in this experiment.

Referring to FIG. 5, a tube 12 is provided in a jacket 11. A sludge supply nozzle 13 and a sewage gas exhaust port 15 are provided in an upper end of the tube 12, and a sludge exhaust port 14 is provided in the bottom portion of the jacket 11. Sludge kneaded in the kneader 1 equipped with a heating jacket is supplied to the tube 12 through the sludge supply nozzle 13. The interior of the tube 12 is maintained at a predetermined temperature by the jacket 11. The sludge is digested and downwardly moved in the tube 12. The sludge thus moved in the tube 12 within a constant period is exhausted from the sludge exhaust port 14. Gas generated by such digestion is exhausted from the sewage gas exhaust port 15 provided in the upper portion of the tube 12.

A tube 12, 160 mm in diameter and 3,500 mm in length, was employed and heated by warm water flowing in the jacket 11 so that its interior was at a temperature of 50° to 55° C. The rate for supplying sludge from the sludge supply nozzle 13 was adjusted so that the sludge passed through the tube 12 in one day.

Within the kneader 1 heated to 50° to 55° C., raw sludge (0.84 kg), which was prepared by heat-treating raw sludge of a solids content of 21 weight % at 160° C. for 30 minutes, was kneaded with seed sludge, i.e., digested sludge (12.0 kg). The sludge mixture thus obtained was fed into the tube 12 once every 6 hours intermittently through the sludge supply nozzle 13.

This bench scale test was operated for 15 days to measure the amount of gas generated by digestion and the methane content in the generated gas. As a result, gas was generated at the rate of about 750 l per 1 kg organic substances contained in the raw sludge. The amount of the gas thus generated in this system was considerably larger than that in an ordinary anaerobic digestion process, which is about 500 l per 1 kg organic substances. The methane content was about 60% which was substantially similar to that in the conventional anaerobic digestion process. It is obvious that the digestion process according to the present invention is excellent also in a bench scale test under conditions further approximate to those for actual operation, since the amount of the generated gas per unit organic substances is significantly improved as compared with that in the conventional digestion process.

Figure 6:
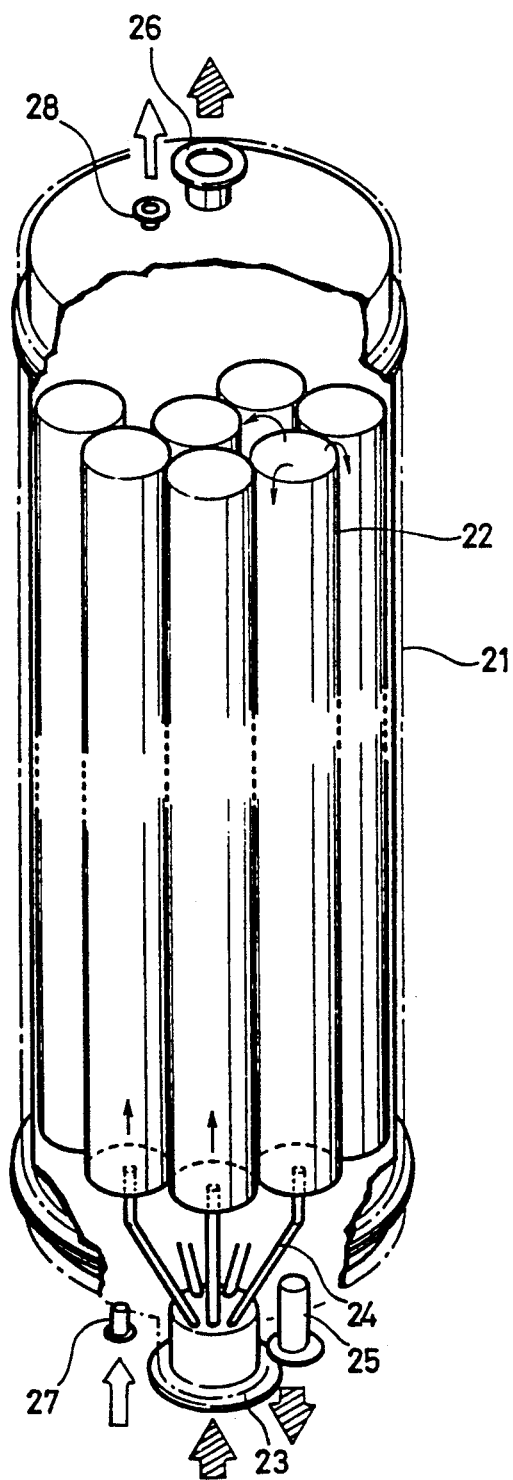
FIG. 6 is a partially fragmented perspective view showing a digestor chamber in the case of applying the present invention to a large scale plant.

FIG. 6 is a partially fragmented perspective view showing an exemplary digestor chamber employed in the case of applying the present invention to a large scale plant. According to the present invention, sludge cannot be digested in a conventional stirring vessel since the sludge has a high viscosity. In one of the effective methods, therefore, the sludge which is kneaded in advance in a kneader is digested during movement in a tube, as shown in FIG. 5. Thus, an apparatus having a plurality of tubes as shown in FIG. 6 can be employed in a large scale plant. Referring to FIG. 6, a plurality of tubes 22 are contained in a jacket 21. The tubes 22 are 0.2 to 1.0 m in diameter and 10 to 30 m in length, for example. The jacket 21 is provided in its bottom portion with a sludge supply port 23, which has sludge distribution nozzles 24 in correspondence with the respective tubes 22. A warm water inlet port 27 and a sludge exhaust port 25 are further provided in the bottom portion of the jacket 21. A sewage gas outlet port 26 for extracting generated gas and a warm water outlet port 28 are provided in an upper portion of the jacket 21.

Sludge supplied from the sludge supply port 23 is pushed into the respective tubes 22 through the sludge distribution nozzles 24. The sludge is gradually upwardly moved within the tubes 22 to overflow the upper ends of the tubes 22, and then downwardly moved along the outer walls of the tubes 22. The sludge thus downwardly moved along the outer walls of the tubes 22 is exhausted from the sludge exhaust port 25, so that a large portion thereof is fed back to the kneader 1 and the remaining portion is disposed.

The sludge is digested during the upward movement within the tubes 22 and the downward movement along the outer walls of the tubes 22. Due to such a system, a long residence time can be ensured even if the tubes 22 are short. Warm water supplied from the warm water inlet port 27 passes through the outer wall of the jacket 21, to be discharged from the warm water outlet port 28. The interior of the jacket 21 is maintained at a predetermined temperature by this warm water.

Through employment of the digestor chamber having a plurality of tubes as shown in FIG. 6, the speed of movement of the sludge within the tubes can be made uniform, thereby to prevent nonuniform movement of the sludge, such as short-circuit flow.

It is to be noted that the digestor chamber shown in FIG. 6 is a mere example of a vessel employable in the present invention, and the present invention is not restricted to the digestor chamber shown in FIG. 6.

Figure 7:
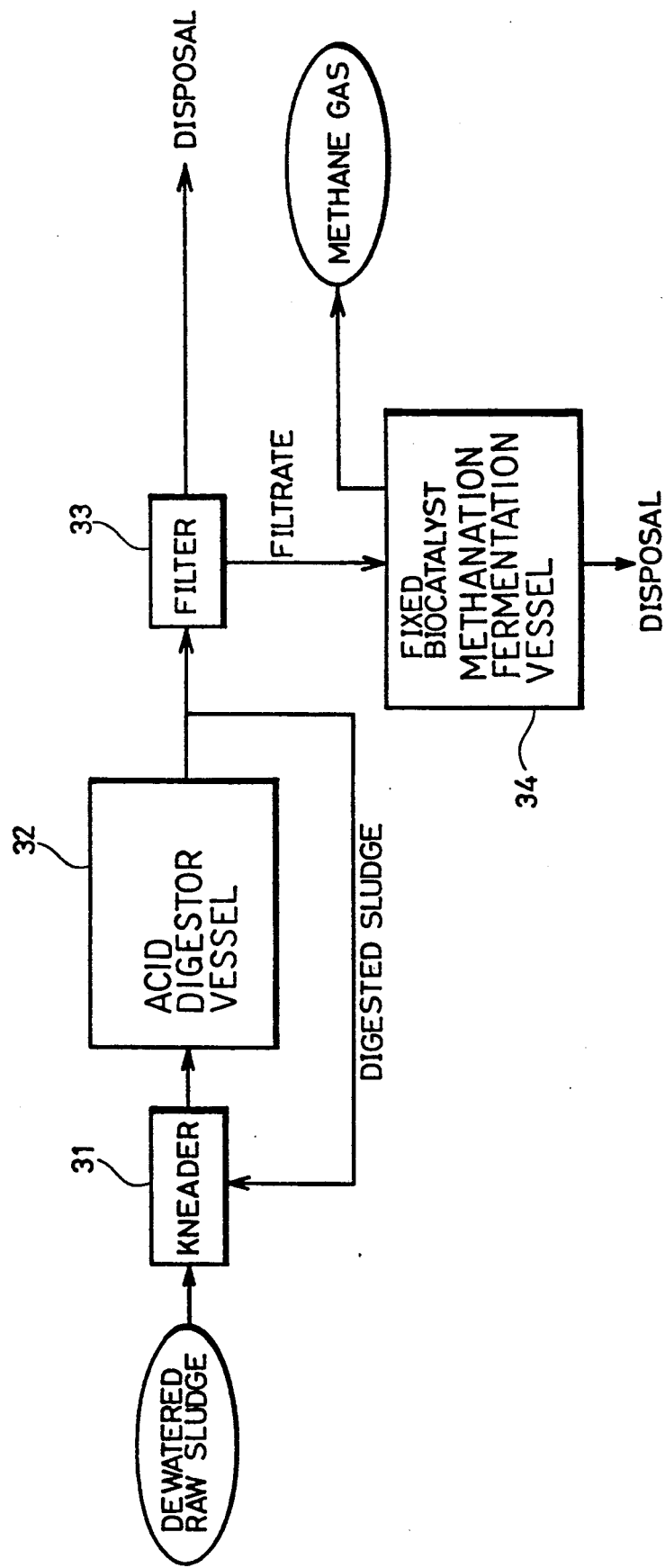
FIG. 7 is a process drawing showing a third embodiment of the present invention.

As hereinabove described, the present invention is also applicable to a two-phase anaerobic digestion process, in which methane fermentation is separated into an acid formation step and a methanation step. FIG. 7 is a process drawing showing an embodiment in which the present invention is applied to such a two-phase anaerobic digestion process. Referring to FIG. 7, dewatered raw sludge is supplied to a kneader 31, to be kneaded with a large portion of digested sludge which is effluent from an acid digester vessel 32. The kneaded sludge is supplied to an acid digestor vessel 32, to be subjected to only an acid formation step. A great portion of the digested sludge after fermentation is fed back to the kneader 31, and the remaining portion is filtered by a filter 33. Organic substances contained in the raw sludge are converted into lower fatty acids, alcohols, carbon dioxide, etc., and solubilized through acid formation fermentation. Thus, such lower fatty acids etc. are dissolved in the filtrate. Solids generated in the filter 33 are disposed. Then the filtrate is supplied to a methanation fermentation vessel 34, in which a biocatalyst for causing methanation fermentation is fixed, to be subjected to methanation fermentation. Biocatalysts for methane fermentation are well known in the art. Methane gas thus generated is extracted and the filtrate passing though the methanation fermentation vessel 34 is disposed. In this embodiment, tube type digestor chambers shown in FIGS. 5 and 6 can be employed as the acid digestor 32.

Furthermore, in this embodiment, raw sludge may be heat-treated in advance before the same is kneaded with seed sludge in a similar manner to the process shown in FIG. 4.

As hereinabove described, the digestion process according to the present invention is also applicable to the two-phase anaerobic digestion process.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An anaerobic digestion process for sewage sludge, comprising an acid formation step causing acid formation fermentation and a methanation step, said process comprising the steps of:
   dewatering raw sewage sludge to provide a solids content therein of at least 10 weight %;
   recirculating a portion of digested sludge resulting from acid formation fermentation;
   adding said dewatered raw sludge to said recirculated portion of digested sludge resulting from acid formation fermentation, the weight ratio of digested sludge to dewatered raw sludge being at least 1:1;
   homogeneously kneading the resulting mixture;
   subjecting the kneaded sludge mixture to acid formation fermentation; and
   subjecting products of the acid formation fermentation to methanation fermentation to generate methane;
   at least one of (a) said dewatered raw sludge prior to addition to said recirculated portion of digested sludge and (b) said kneaded sludge mixture in said acid formation fermentation step being subjected to thermal treatment at a temperature not less than about 50° C.

2. A process in accordance with claim 1, wherein said dewatering step provides a solids content of at least 15 weight%.

3. A process in accordance with claim 1, wherin said dewatering step provides a solids content of at least 20 weight %.

4. A process in accordance with claim 1, wherein the dewatered raw sludge is subjected to a thermal treatment at a temperature not less than about 50° C. prior to addition to said recirculated portion of digested sludge.

5. A process in accordance with claim 1, wherein the dewatered raw sludge is subjected to a thermal treatment at a temperature of from about 60° C. to about 180° C. prior to addition to said recirculated portion of digested sludge.

6. A process in accordance with claim 1, wherein during said acid formation fermentation, the kneaded sludge mixture is subjected to thermal treatment at a temperature not less than about 50° C.

7. A process in accordance with claim 6, wherein during said acid formation fermentation, the kneaded sludge mixture is subjected to thermal treatment at a temperature of from about 50° C. to about 55° C.

8. A process in accordance with claim 1, wherein said methanation step comprises the substeps of:
   separating said products resulting from said acid formation fermentation of said kneaded sludge mixture by filtering said products after said acid formation fermentation to produce a filtrate, and
   generating methane from said filtrate by passing the filtrate through a fixed biocatalyst.

* * * * *